US009446008B2

(12) United States Patent
Reinhold et al.

(10) Patent No.: US 9,446,008 B2
(45) Date of Patent: *Sep. 20, 2016

(54) SEMISOLID AQUEOUS PHARMACEUTICAL COMPOSITION CONTAINING TAPENTADOL (75) Inventors: Ulrich Reinhold, Aachen (DE); Marc Schiller, Aachen (DE); Eva Wulsten, Willich (DE); Sabine Karine Katrien Inghelbrecht, Beerse (BE); Roger Carolus Augusta Embrechts, Beerse (BE); Ulrich Feil, Aschaffenburg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,837

(22) Filed: Mar. 2, 2012

(65) Prior Publication Data
US 2012/0225950 A1    Sep. 6, 2012

Related U.S. Application Data (60) Provisional application No. 61/449,329, filed on Mar. 4, 2011.

(30) Foreign Application Priority Data

May 3, 2011 (EP) ..................................... 11003603

(51) Int. Cl.
A61K 9/00     (2006.01)
A61K 31/137   (2006.01)
A61K 47/14    (2006.01)
A61K 9/107    (2006.01)

(52) U.S. Cl.
CPC ........... *A61K 31/137* (2013.01); *A61K 9/0014* (2013.01); *A61K 9/107* (2013.01); *A61K 47/14* (2013.01)

(58) Field of Classification Search
None
See application file for complete search history.

(56) References Cited

U.S. PATENT DOCUMENTS

| 4,775,678 | A | * | 10/1988 | Su et al. ........................ 514/396 |
| 6,183,758 | B1 | * | 2/2001 | Scott ............................ 424/401 |
| 6,248,737 | B1 | | 6/2001 | Buschmann et al. |
| 6,399,087 | B1 | | 6/2002 | Zhang et al. |
| 2003/0191187 | A1 | | 10/2003 | Lee et al. |
| 2003/0203055 | A1 | | 10/2003 | Rao et al. |
| 2004/0180915 | A1 | | 9/2004 | Gonzales et al. |
| 2005/0176790 | A1 | | 8/2005 | Bartholomaus et al. |
| 2005/0186267 | A1 | | 8/2005 | Thompson et al. |
| 2006/0111382 | A1 | | 5/2006 | Shafer et al. |
| 2007/0128412 | A1 | | 6/2007 | Tso et al. |
| 2007/0213405 | A1 | | 9/2007 | Fischer et al. |
| 2008/0039405 | A1 | * | 2/2008 | Langley et al. ................. 514/29 |
| 2008/0269326 | A1 | | 10/2008 | Christoph et al. |
| 2009/0012180 | A1 | | 1/2009 | Lange et al. |
| 2010/0227921 | A1 | | 9/2010 | Franklin et al. |
| 2010/0272815 | A1 | | 10/2010 | Khunt et al. |
| 2010/0311842 | A1 | | 12/2010 | Christoph et al. |
| 2011/0190267 | A1 | * | 8/2011 | Franklin et al. ......... 514/212.01 |
| 2012/0201891 | A1 | * | 8/2012 | Cottrell et al. ............... 424/485 |
| 2012/0270848 | A1 | * | 10/2012 | Mannion et al. ............. 514/171 |
| 2013/0273152 | A1 | | 10/2013 | Draget et al. |

FOREIGN PATENT DOCUMENTS

| CA | 2 725 635 | A1 | 9/2002 |
| CA | 2439269 | C | 11/2011 |
| CN | 101495447 | A | 7/2009 |
| EA | 201300988 | A1 | 6/2014 |
| EP | 0 693 475 | A1 | 1/1996 |
| EP | 2 117 525 | | 11/2009 |
| JP | 2004-527491 | A | 9/2004 |
| JP | 2010520907 | A | 6/2010 |
| RU | 2 309 942 | C2 | 11/2007 |
| WO | WO 02/067651 | A2 | 9/2002 |
| WO | WO 03/035053 | A1 | 5/2003 |
| WO | WO 2006/002886 | A1 | 1/2006 |
| WO | WO 2006/116626 | A2 | 11/2006 |
| WO | WO 2007/128412 | A1 | 11/2007 |
| WO | WO 2007/128413 | A1 | 11/2007 |
| WO | WO 2008/012283 | A1 | 1/2008 |
| WO | WO 2008/110323 | A1 | 9/2008 |
| WO | WO 2009/067703 | A2 | 5/2009 |
| WO | WO 2009/092601 | A1 | 7/2009 |
| WO | WO 2010/096045 | A1 | 8/2010 |
| WO | WO 2011/128630 | A2 | 10/2011 |
| WO | WO 2012/119729 | A1 | 9/2012 |

OTHER PUBLICATIONS

Lippincott et al. (Fluids & Electrolytes—An Incredibly Easy Pocket Guide, (2006), Lippincott, Williams, and Wilkins, Ambler PA, pp. 179-181,).*
Tamanai-Shacoori et al (2007; "The Antibacterial Activity of Tramadol Against Bacteria Associated with Infectious Complications After Local or Regional Anesthesia." Anesth Analg,105:524-7.*
Mehta et al (Mar. 2010; # 228 Tapentadol.*
Tzschentke et al., "Tapentadol Hydrochloride", Analgesic, Mu-Opioid Receptor Agonist, Noradrenaline Reuptake Inhibitor, Drugs of the Future, vol. 31, No. 12, pp. 1053-1061, Dec. 2006, XP002660111.
Ho et al., "In Vitro Effects Preservatives in Nasal Sprays on Human Nasal Epithelial Cells", American Journal of Rhinology, 2008, vol. 22, No. 2, pp. 125-129.
Hong et al., "Allergy to Ophthalmic Preservatives", Current Opinion in Allergy and Clinical Immunology, 2009, vol. 9, pp. 447-453.
Soni et al., "Safety Assessment of Propyl Paraben: a Review of the Published Literature", Food and Chemical Toxicology, 2001, vol. 39, No. 6, pp. 513-532.

(Continued)

*Primary Examiner* — Snigdha Maewall
(74) *Attorney, Agent, or Firm* — Crowell & Moring LLP (57) ABSTRACT A semisolid aqueous pharmaceutical composition containing tapentadol or a physiologically acceptable salt thereof.

14 Claims, 1 Drawing Sheet

(56) References Cited

OTHER PUBLICATIONS

Oishi, "Effects of Propyl Paraben on the Male Reproductive System", Food and Chemical Toxicology, 2002, vol. 40, No. 12, pp. 1807-1813.
Soni etal., "Safety Assessment of Esters of p-hydroxybenzoic Acid (parabens)", Food and Chemical Toxicology, 2005, vol. 43, No. 7, pp. 985-015.
European Search Report dated Oct. 12, 2011.
Co-pending U.S. Appl. No. 13/410,768, filed Mar. 2, 2012.
Co-pending U.S. Appl. No. 13/410,945, filed Mar. 2, 2012.
Tamanai-Shacoori et al (2007) "The Antibacterial Activity of Tramadol Against Bacteria Associated with Infectious Complications After Local or Regional Anesthesia." Anesth Analg, 105: 524-7.
Mehta et al (Mar. 20210) "# 228 Tapentadol." Retrieved on Oct. 16, 2014. Retrieved from the Internet <URL: http://www.eperc.mcw.edu/EPERC/FastFactsIndex/ff_228.htm>.
American Academy of Pediatrics (Feb. 2, 1997). "Inactive Ingredients in Pharmaceutical Products: Update (Subject Review)." Pediatrics, 99: 268-278.
Liu, "Pharmacology and clinical application of analgesic tapentadol with a dual mode of action," Pain Clin J., 2008, pp. 293-298, vol. 4, No. 4.
Thomas Christoph et al., "Tapentadol, but not morphine selectively inhibits disease-related thermal hyperalgesia in a mouse model of diabetic neuropathic pain", Neuroscience Letters 470 (2010) pp. 91-94.
Thomas M. Tzschentke et al., "(-)-(1R,2R)-3-(3-Dimethylamino-1-ethyl-2-methyl-propyl)-phenol Hydrochloride (Tapentadol HCl): a Novel p-Opioid Receptor Agonist/Norepinephrine Reuptake Inhibitor with Broad-Spectrum Analgesic Properties", the Journal of Pharmacology and Experimental Therapeutics (2007) vol. 323, No. 1, pp. 265-276.
Wolfgang Schroeder et al., "Differential contribution of opioid and noradrenergic mechanisms of tapentadol in rat models of nociceptive and neuropathic pain", European Journal of Pain 14 (2010) pp. 814-821.
Copending U.S. Appl. No. 14/981,223, filed Dec. 28, 2015, "Parenteral Administration of Tapentadol".

\* cited by examiner

SEMISOLID AQUEOUS PHARMACEUTICAL COMPOSITION CONTAINING TAPENTADOL

CROSS REFERENCE TO RELATED APPLICATIONS

This application claims priority from U.S. provisional patent application No. 61/449,329, filed Mar. 4, 2011, the entire disclosure of which is incorporated herein by reference. Priority is also claimed based on European patent application no. EP 11 003 603.5, filed May 3, 2011, the entire disclosure of which is likewise incorporated herein by reference.

BACKGROUND OF THE INVENTION

The invention relates to a semisolid aqueous pharmaceutical composition containing tapentadol or a physiologically acceptable salt thereof.

Tapentadol is a centrally-acting analgesic with a dual mode of action as an agonist at the μ-opioid receptor and as a norepinephrine reuptake inhibitor (cf. T. M. Tzschentke et al., Drugs of the future, 2006, 12, 1053-1061). Solid oral dosage forms of tapentadol are known from the prior art, e.g. WO 02/67651, WO 03/035053, WO 2006/002886, WO 2007/128412, WO 2007/128413, WO 2008/110323, WO 2009/092601, WO 2009/067703, and US2010-272815. WO 2008/110323 discloses a composition for parenteral administration of 20 g (1R,2R)-3-(3-dimethylamino-1-ethyl-2-methyl-propyl)-phenol hydrochloride in 1 L water for injection purposes which has been isotonized by addition of NaCl.

However, solid oral dosage forms containing tapentadol are not satisfactory in every respect and there is a demand of pharmaceutical formulations which have advantages compared to the known solid oral dosage forms.

For instance, the pain may be caused by a topical effect that does not require systemic treatment. In this case, systemic side effects may be avoided when tapentadol is applied topically and/or locally. Typically, the drug may be applied directly to the source of pain in a high dosage, thereby keeping the burden to entire organism to a minimum. Consequently, there is a demand of pharmaceutical formulations containing tapentadol for topical and/or local administration.

The stability of the active ingredient in the final product is a primary concern to the formulator. In general, drug substances are less stable in aqueous media than solid dosage forms, and it is important to properly stabilize and preserve liquid aqueous formulations such as solutions, suspensions, and emulsions. Acid-base reactions, acid or base catalysis, oxidation, and reduction can occur in these products. These reactions can arise from drug substance-ingredient interactions, ingredient-ingredient interactions or container-product interactions. For pH sensitive compounds, any of these interactions may alter the pH and may cause precipitation.

Oxidative labile drug substances or vitamins, essential oils, and almost all fats and oils can be oxidized by autooxidation. Such reactions can be initiated by heat, light, peroxides, or other labile compounds or heavy metals such as copper or iron.

The effect of trace metals can be minimized by using chelating agents such as EDTA. Antioxidants may retard or delay oxidation by rapidly reacting with free radicals as they are formed (quenching). Common antioxidants include propyl, octyl and dodecylesters of gallic acid, butylated hydroxyanisole (BHA), butylated hydroxytoluene (BHT), ascorbic acid, sodium ascorbate, monothioglycerol, potassium or sodium metabisulfite, propionic acid, propyl gallate, sodium bisulfite, sodium sulfite, and the tocopherols or vitamin E.

In addition to stabilization of pharmaceutical preparations against chemical and physical degradation, liquid and semisolid preparations, particularly multiple dose preparations, must usually be protected against microbial contamination. In contrast to solid preparations, aqueous solutions, syrups, emulsions, and suspensions often provide excellent growth media for microorganisms such as molds, yeast, and bacteria (e.g. *Pseudomonas Aeruginosa, E. Coli, Salmonella* spp., *Staphylococcus aureus, Candida albicans, Aspergillus niger*). Contamination by these microorganisms may occur during manufacturing or when a dose is taken from a multiple dose formulation. Growth of the microorganisms occurs when a sufficient amount of water is present in the formulation. Biphasic systems of the O/W-type are especially prone to be excellent breeding grounds for microorganisms.

Ophthalmic and injectable preparations are typically sterilized by autoclaving or filtration. However, many of them require the presence of an antimicrobial preservative to maintain aseptic conditions throughout their stated shelf life, specifically for multiple dose preparations.

When a preservative is required, its selection is based upon several considerations, in particular the site of use whether internal, external or ophthalmic (for further details it can be referred to e.g. Remington, The Science and Practice of Pharmacy, 21$^{st}$ edition, Lippincott Williams & Wilkins, 2005).

Many liquid and semisolid formulations, particularly multiple dose formulations and/or O/W-formulations, contain parabens as preservatives, e.g. methyl paraben (methyl-4-hydroxybenzoate) and propyl paraben (propyl-4-hydroxybenzoate). For example, in the Federal Republic of Germany semi-solid formulations containing analgesics such as ibuprofen and parabens are commercialized under the trademarks: Dolgit®, Ibutop® and Elacur®.

Because of the number of excipients and additives in pharmaceutical formulations, it is recommended all the ingredients be listed on the container to reduce the risks that confront hypersensitive patients when these products are administered.

Other commercialized pharmaceutical formulations contain sorbic acid or its potassium salt (e.g. Mobilat®) or benzalkonium chloride as preservative. Recently, side effects resulting from mucosal damage caused by benzalkonium chloride and potassium sorbate were reported (cf. C. Y. Ho et al., Am J Rhinol. 2008, 22(2), 125-9). As far as hypersensitivity reactions of preservatives in topical ophthalmic therapies are concerned, quaternary ammoniums (benzalkonium chloride) are commonly associated with irritant toxic reactions whereas the organomercurials (thimerosal) and the alcohols (chlorobutanol) have high associations, respectively, with allergic responses (cf. J. Hong et al., Curr Opin Allergy Clin Immunol. 2009, 9(5), 447-53). Parabens have been implicated in numerous cases of contact sensitivity associated with cutaneous exposure (cf. M. G. Soni et al., Food Chem. Toxicol. 2001, 39(6), 513-32) and have been reported to to exert a weak estrogenic activity (cf. S. Oishi, Food Chem. Toxicol. 2002, 40(12), 1807-13 and M. G. Soni et al., Food Chem. Toxicol. 2005, 43(7), 985-015).

Due to these undesired side effects of known preservatives, it is desirable to provide pharmaceutical compositions for topical and/or local administration that exhibit a sufficient shelf-life in the absence of preservatives or at least in the presence of comparatively low quantities thereof.

SUMMARY OF THE INVENTION

It is an object of the invention to provide pharmaceutical formulations of tapentadol that have advantages over the pharmaceutical formulations of the prior art.

A further object of the invention is to provide pharmaceutical formulations containing tapentadol or a physiologically acceptable salt thereof which do not have the aforementioned preservative based side effects, such as allergic reactions, typically observed with pharmaceutical formulations containing preservatives.

An additional object of the invention is to provide pharmaceutical formulations which are suitable for topical and/or local administration of tapentadol.

These and other objects are achieved by the invention as described and claimed hereinafter.

It has been surprisingly found that tapentadol as such exhibits preservative properties and thus, when formulating comparatively labile compositions, particularly aqueous liquid or semisolid compositions, preservatives can be completely omitted or at least need to be present in comparatively low amounts in order to achieve the stated shelf-life.

A first aspect of the invention relates to a semisolid aqueous pharmaceutical composition containing tapentadol.

The term "pharmaceutical composition" includes any pharmaceutical preparation or formulation that is customized for being administered to a human being or animal.

For the purpose of this application the term "tapentadol" includes the free base ((1R,2R)-3-(3-dimethylamino-1-ethyl-2-methyl-propyl)-phenol) as well as any physiologically acceptable salt thereof, particularly the hydrochloride ((1R,2R)-3-(3-dimethylamino-1-ethyl-2-methyl-propyl)-phenol hydrochloride). Thus, unless expressly states otherwise, the term "tapentadol" does not only refer to the free base but also to any physiologically acceptable salt. Further, unless expressly stated otherwise, all amounts, contents and concentrations are equivalents related to tapentadol free base.

DETAILED DESCRIPTION OF EMBODIMENTS

In a preferred embodiment, the content of tapentadol is within the range of from 0.01 to 50 wt.-%, more preferably 0.05 to 45 wt.-%, still more preferably 0.1 to 40 wt.-%, yet more preferably 0.5 to 35 wt.-%, most preferably 1.0 to 30 wt.-% and in particular 5.0 to 25 wt.-%, based on the total weight of the composition.

In another preferred embodiment, the content of tapentadol is within the range of from 0.0001 to 5.0 wt.-%, more preferably 0.0005 to 4.5 wt.-%, still more preferably 0.001 to 4.0 wt.-%, yet more preferably 0.005 to 3.5 wt.-%, most preferably 0.01 to 3.0 wt.-% and in particular 0.05 to 2.5 wt.-%, based on the total weight of the composition. In a preferred embodiment, the content of tapentadol is within the range of from 0.01 to 3.0 wt.-%, more preferably 0.05 to 2.8 wt.-%, still more preferably 0.1 to 2.6 wt.-%, yet more preferably 0.2 to 2.4 wt.-%, most preferably 0.3 to 2.2 wt.-% and in particular 0.4 to 2.0 wt.-%, based on the total weight of the composition. Preferably, the content of tapentadol is equal or less than 5.0 wt.-%, based on the total weight of the composition.

In a preferred embodiment, the content of tapentadol is within the range of 0.4±0.35 wt.-%, more preferably 0.4±0.3 wt.-%, still more preferably 0.4±0.2 wt.-%, yet more preferably 0.4±0.15 wt.-%, most preferably 0.4±0.1 wt.-%, and in particular 0.4±0.05 wt.-%, based on the total weight of the composition.

In another preferred embodiment, the content of tapentadol is within the range of 0.6±0.5 wt.-%, more preferably 0.6±0.4 wt.-%, still more preferably 0.6±0.3 wt.-%, yet more preferably 0.6±0.2 wt.-%, most preferably 0.6±0.1 wt.-%, and in particular 0.6±0.05 wt.-%, based on the total weight of the composition.

In still another preferred embodiment, the content of tapentadol is within the range of 0.8±0.6 wt.-%, more preferably 0.8±0.5 wt.-%, still more preferably 0.8±0.4 wt.-%, yet more preferably 0.8±0.3 wt.-%, most preferably 0.8±0.2 wt.-%, and in particular 0.8±0.1 wt.-%, based on the total weight of the composition.

In yet another preferred embodiment, the content of tapentadol is within the range of 1.0±0.9 wt.-%, more preferably 1.0±0.7 wt.-%, still more preferably 1.0±0.5 wt.-%, yet more preferably 1.0±0.3 wt.-%, most preferably 1.0±0.2 wt.-%, and in particular 1.0±0.1 wt.-%, based on the total weight of the composition.

In a further preferred embodiment, the content of tapentadol is within the range of 1.2±1.0 wt.-%, more preferably 1.2±0.8 wt.-%, still more preferably 1.2±0.6 wt.-%, yet more preferably 1.2±0.4 wt.-%, most preferably 1.2±0.2 wt.-%, and in particular 1.2±0.1 wt.-%, based on the total weight of the composition.

In a preferred embodiment, the content of tapentadol amounts to at least 0.05, at least 0.10 or at least 0.15 wt.-%, more preferably at least 0.20, at least 0.25 or at least 0.30 wt.-%, still more preferably at least 0.35, at least 0.40 or at least 0.45 wt.-%, yet more preferably at least 0.50, at least 0.55 or at least 0.60 wt.-%, most preferably at least 0.65, at least 0.70 or at least 0.75 wt.-%, and in particular at least 0.80, at least 0.85 or at least 0.90 wt.-%, based on the total weight of the composition.

Preferably, the tapentadol is homogeneously distributed in the composition according to the invention. The content of tapentadol of two segments of the composition having a volume of 0.1 mL each, deviate from one another by preferably not more than ±10%, more preferably not more than more than ±7.5%, still more preferably not more than ±5.0%, most preferably not more than ±2.5%, and in particular not more than ±1.0%.

Preferably, the composition according to the invention is characterized by a comparatively homogeneous distribution of density. Preferably, the densities of two segments of the pharmaceutical composition having a volume of 0.1 mL each, deviate from one another by not more than ±10%, more preferably not more than more than ±7.5%, still more preferably not more than ±5.0%, most preferably not more than ±2.5%, and in particular not more than ±1.0%.

The composition according to the invention is aqueous. For the purpose of this application, the term "aqueous" means that its water content is preferably above the typical water content of solid pharmaceutical compositions which are humidified from the atmosphere due to the more or less pronounced hygroscopic properties of their constituents.

Preferably, the water content of the composition is at least 0.5 wt.-%, more preferably at least 1.0 wt.-%, still more preferably at least 2.0 wt.-%, yet more preferably at least 3.0 wt.-%, most preferably at least 4.0 wt.-% and in particular at least 5.0 wt.-%, based on the total weight of the composition.

In a preferred embodiment, the water content of the composition is within the range of 35±30 wt.-%, more preferably 35±25 wt.-%, still more preferably 35±20 wt.-%, yet more preferably 35±15 wt.-%, most preferably 35±10 wt.-% and in particular 35±5 wt.-%, based on the total weight of the composition.

In another preferred embodiment, the water content of the composition is within the range of 45±30 wt.-%, more preferably 45±25 wt.-%, still more preferably 45±20 wt.-%, yet more preferably 45±15 wt.-%, most preferably 45±10 wt.-% and in particular 45±5 wt.-%, based on the total weight of the composition.

In still another preferred embodiment, the water content of the composition is within the range of 55±30 wt.-%, more preferably 55±25 wt.-%, still more preferably 55±20 wt.-%, yet more preferably 55±15 wt.-%, most preferably 55±10 wt.-% and in particular 55±5 wt.-%, based on the total weight of the composition.

In yet another preferred embodiment, the water content of the composition is within the range of 65±30 wt.-%, more preferably 65±25 wt.-%, still more preferably 65±20 wt.-%, yet more preferably 65±15 wt.-%, most preferably 65±10 wt.-% and in particular 65±5 wt.-%, based on the total weight of the composition.

The pharmaceutical composition according to the invention is semisolid at room temperature. A skilled person knows how to distinguish semisolid pharmaceutical compositions from solid pharmaceutical compositions and from liquid pharmaceutical compositions. The term "semisolid" is well accepted in the art. For the purpose of this application, the term "semisolid" preferably has the meaning as used in the Eur. Ph. Preferably, the semisolid preparation becomes liquid at a temperature of at most 100° C., more preferably of at most 95° C., still more preferably of at most 90° C., yet more preferably of at most 85° C., most preferably of at most 80° C. and in particular of at most 75° C.

According to the Eur. Ph. semisolid preparations can be systematically divided into oinments (hydrophobic, hydrophilic and absorption ointments), creams (hydrophobic and hydrophilic), gels (hydrophobic and hydrophilic), pastes, poultices and plasters. Thus, the composition according to the invention is preferably selected from the group consisting of oinments, creams, gels, pastes, poultices and plasters.

Ointments are lipid-based semisolid preparations which do not necessarily contain an aqueous phase and appear homogeneous. In simplified terms, they are characterized as single-phase preparations, although liquid and/or solid particles may be dispersed therein. Typical base formulations for hydrophobic ointments contain hard paraffin, soft paraffin, vegetable oils, animal fats, hydrogenated oils, synthetic oily materials, partially synthetic glycerides and/or waxes. Hydrophobic ointments can only absorb small amounts of water. Hydrophilic ointments and absorption ointments further contain emulsifiers that increase their potency to absorb water. Hydrophilic ointments are based on formulations that are soluble in water. They often contain a polyethylene glycol.

Creams are bi-phasic or multiple-phase systems that contain an aqueous and lipid phase. They often have an opaque appearance as contrasted with translucent ointments. Creams contain at least one surfactant (emulsifier) whose hydrophilicity determines whether the cream is hydrophobic (e.g., w/o-type), hydrophilic (e.g., o/w-type) or ambiphilic. A cream's phase characteristics are often complex. For instance, creams may contain more phases than only the aqueous and lipid phase, e.g. an aqueous phase and two lipid phases. Or it may further contain solid particles or the lipid phase may be solid itself. Therefore, creams are usually not classified as emulsions. They may, however, be referred to as emulsoid.

Gels are semisolid systems in which a liquid is solidified by a gelling agent which forms three-dimensional cross-linked network within the liquid. The liquid may be aqueous (hydrophobic gel, oleogel) or lipid-based (hydrophilic gel, hydrogel). Gels typically exhibit no flow when in the steady-state.

Creams and ointments may also contain thickening agents and the classification is not in each and every case unambigous. For instances, there are semisolid systems that can both be classified as o/w-creams or hydrogels, and are thus also referred to as emulsion gels.

Pastes are lipid-based preparations which contain a high amount of solid particles dispersed therein. They usually contain only a small amount of water. Preparations of this type that contain a high amount of water are usually referred to as poultices.

In common parlance, free-running aqueous multiple-phase preparations that are suspensions of solid particles in hydrophilic solvents or emulsions are also referred to as lotions.

Preferably, the composition according to the invention is selected from the group consisting of ointments, creams, magmas, gels, emulsions, suspensions, lotions, liniments, pastes, poultices, suspension gels and emulsion gels.

In a preferred embodiment, the composition according to the invention is an emulsoid preparation such as a cream or lotion. The emulsoid preparation may be hydrophilic, hydrophobic or amphiphilic.

For the purpose of this application, the term "hydrophilic emulsoid preperation" refers to any emulsoid preparation in which the aqueous phase represents the external phase, including bi-phasic preparations of the w/o-type and multiple-phase preparations of the w/o/w-type.

For the purpose of this application, the term "hydrophobic emulsoid preparation" refers to any bi-phasic emulsoid preparation in which the lipid phase represents the external phase, including biphasic preparations of the w/o-type.

Preferably, the emulsoid preparation is hydrophilic. In particular, the emulsoid preparation is of the o/w-type (oil-in-water) or w/o/w-type (w/o emulsoid preparation in water).

In another preferred embodiment, the composition according to the invention is a suspensoid preparation, preferably selected from the group consisting of sustained release suspensions, gels and magmas, and lotions.

In a preferred embodiment, the aqueous composition according to the invention is a single phase formulation. In another preferred embodiment, the composition according to the invention is a two-phase or multi-phase formulation. Preferably, the composition contains at least one aqueous phase and at least one lipid phase.

In a preferred embodiment, the aqueous phase and the lipid phase form a bicoherent system.

In another preferred embodiment, the aqueous phase and the lipid phase form an emulsoid or suspendoid system, in which they may independently of each other be present as dispersed phase and/or coherent phase.

If the emulsoid system contains a solid phase, two or three coherent phases may be present. For example, the lipid phase may be dispersed in an aqueous phase and contain a second aqueous phase dispersed therein (w/o/w-type). Preferably, the emulsoid system contains at least one aqueous coherent phase.

The semisolid aqueous pharmaceutical composition according to the invention contains tapentadol. Preferably, the tapentadol is dispersed in the composition. In particular, the tapentadol is dissolved in an aqueous phase, which may either represent the composition's single phase or be part of multiple-phase system.

In a preferred embodiment, the aqueous phase of the composition has a pH value of at least 5.50, more preferably at least 5.75, still more preferably at least 6.00, yet more preferably at least 6.25, even more preferably at least 6.50, most preferably at least 6.75, and in particular at least 7.00.

In a preferred embodiment, the pH value of the aqueous phase of the composition is at least 5.4, more preferably at least 5.5, still more preferably at least 5.6, yet more preferably at least 5.7, most preferably at least 5.8 and in particular at least 5.9. Preferably, the pH value is within the range of from 5.4 to 6.5, more preferably 5.5 to 6.3, still more preferably 5.4 to 6.0.

In a preferred embodiment, the pH value is within the range of 5.7±0.3, more preferably 5.7±0.25, still more preferably 5.7±0.2, most preferably 5.7±0.15, and in particular 5.7±0.1.

In a preferred embodiment, the pH value is within the range of 6.0±0.6, more preferably 6.0±0.5, still more preferably 6.0±0.4, even more preferably 6.0±0.3, most preferably 6.0±0.2, and in particular 6.0±0.1.

In a preferred embodiment, the pH value is within the range of 6.5±1.0, more preferably 6.5±0.9, still more preferably 6.5±0.8, yet more preferably 6.5±0.7, even more preferably 6.5±0.6 or 6.5±0.5, most preferably 6.5±0.4 or 6.5±0.3, and in particular 6.5±0.2 or 6.5±0.1.

In a preferred embodiment, the pH value is within the range of 7.0±1.4 or 7.0±1.3, more preferably 7.0±1.2 or 7.0±1.1, still more preferably 7.0±1.0 or 7.0±0.9, yet more preferably 7.0±0.8 or 7.0±0.7, even more preferably 7.0±0.6 or 7.0±0.5, most preferably 7.0±0.4 or 7.0±0.3, and in particular 7.0±0.2 or 7.0±0.1.

In a preferred embodiment, the pH value is within the range of 7.5±1.4 or 7.5±1.3, more preferably 7.5±1.2 or 7.5±1.1, still more preferably 7.5±1.0 or 7.5±0.9, yet more preferably 7.5±0.8 or 7.5±0.7, even more preferably 7.5±0.6 or 7.5±0.5, most preferably 7.5±0.4 or 7.5±0.3, and in particular 7.5±0.2 or 7.5±0.1.

In a preferred embodiment, the pH value is within the range of 8.0±1.4 or 8.0±1.3, more preferably 8.0±1.2 or 8.0±1.1, still more preferably 8.0±1.0 or 8.0±0.9, yet more preferably 8.0±0.8 or 8.0±0.7, even more preferably 8.0±0.6 or 8.0±0.5, most preferably 8.0±0.4 or 8.0±0.3, and in particular 8.0±0.2 or 8.0±0.1.

In a preferred embodiment, the pH value is within the range of 8.5±1.4 or 8.5±1.3, more preferably 8.5±1.2 or 8.5±1.1, still more preferably 8.5±1.0 or 8.5±0.9, yet more preferably 8.5±0.8 or 8.5±0.7, even more preferably 8.5±0.6 or 8.5±0.5, most preferably 8.5±0.4 or 8.5±0.3, and in particular 8.5±0.2 or 8.5±0.1.

It has been surprisingly found that tapentadol exhibits a pH-dependent antimicrobial effect. Thus, the pH value of the aqueous phase of the composition according to the invention is preferably adjusted to a value within the physiologically acceptable range where the antimicrobial effect of tapentadol is maximized.

In a preferred embodiment, the concentration of tapentadol is equal or below 20 mg/mL, based on the total volume of all aqueous phases within the composition.

In a preferred embodiment, the concentration of tapentadol is within the range of 17.5±6 mg/mL, more preferably 17.5±5 mg/mL, still more preferably 17.5±4 mg/mL, yet more preferably 17.5±3 mg/mL, most preferably 17.5±2 mg/mL, and in particular 17.5±1 mg/mL, based on the total volume of all aqueous phases within the composition.

In another preferred embodiment, the concentration of tapentadol is within the range of 15±6 mg/mL, more preferably 15±5 mg/mL, still more preferably 15±4 mg/mL, yet more preferably 15±3 mg/mL, most preferably 15±2 mg/mL, and in particular 15±1 mg/mL, based on the total volume of all aqueous phases within the composition.

In still another preferred embodiment, the concentration of tapentadol is within the range of 12.5±6 mg/mL, more preferably 12.5±5 mg/mL, still more preferably 12.5±4 mg/mL, yet more preferably 12.5±3 mg/mL, most preferably 12.5±2 mg/mL, and in particular 12.5±1 mg/mL, based on the total volume of all aqueous phases within the composition.

In still another preferred embodiment, the concentration of tapentadol is within the range of 10±6 mg/mL, more preferably 10±5 mg/mL, still more preferably 10±4 mg/mL, yet more preferably 10±3 mg/mL, most preferably 10±2 mg/mL, and in particular 10±1 mg/mL, based on the total volume of all aqueous phases within the composition.

In yet another preferred embodiment, the concentration of tapentadol is within the range of 7.5±6 mg/mL, more preferably 7.5±5 mg/mL, still more preferably 7.5±4 mg/mL, yet more preferably 7.5±3 mg/mL, most preferably 7.5±2 mg/mL, and in particular 7.5±1 mg/mL, based on the total volume of all aqueous phases within the composition.

In a further preferred embodiment, the concentration of tapentadol is within the range of 4±3 mg/mL, more preferably 4±2.5 mg/mL, still more preferably 4±2 mg/mL, yet more preferably 4±1.5 mg/mL, most preferably 0.6±1 mg/mL, and in particular 0.6±0.05 mg/mL, based on the total volume of all aqueous phases within the composition.

In another preferred embodiment, the concentration of tapentadol is equal or above 20 mg/mL, based on the total volume of all aqueous phases within the composition.

In a preferred embodiment, the concentration of tapentadol is within the range of 22.5±6 mg/mL, more preferably 22.5±5 mg/mL, still more preferably 22.5±4 mg/mL, yet more preferably 22.5±3 mg/mL, most preferably 22.5±2 mg/mL, and in particular 22.5±1 mg/mL, based on the total volume of all aqueous phases within the composition.

In another preferred embodiment, the concentration of tapentadol is within the range of 25±6 mg/mL, more preferably 25±5 mg/mL, still more preferably 25±4 mg/mL, yet more preferably 25±3 mg/mL, most preferably 25±2 mg/mL, and in particular 25±1 mg/mL, based on the total volume of all aqueous phases within the composition.

In another preferred embodiment, the concentration of tapentadol is within the range of 27.5±6 mg/mL, more preferably 27.5±5 mg/mL, still more preferably 27.5±4 mg/mL, yet more preferably 27.5±3 mg/mL, most preferably 27.5±2 mg/mL, and in particular 27.5±1 mg/mL, based on the total volume of all aqueous phases within the composition.

In still another preferred embodiment, the concentration of tapentadol is within the range of 30±6 mg/mL, more preferably 30±5 mg/mL, still more preferably 30±4 mg/mL, yet more preferably 30±3 mg/mL, most preferably 30±2 mg/mL, and in particular 30±1 mg/mL, based on the total volume of all aqueous phases within the composition.

In still another preferred embodiment, the concentration of tapentadol is within the range of 32.5±6 mg/mL, more preferably 32.5±5 mg/mL, still more preferably 32.5±4 mg/mL, yet more preferably 32.5±3 mg/mL, most preferably 32.5±2 mg/mL, and in particular 32.5±1 mg/mL, based on the total volume of all aqueous phases within the composition.

In yet another preferred embodiment, the concentration of tapentadol is within the range of 35±6 mg/mL, more preferably 35±5 mg/mL, still more preferably 35±4 mg/mL, yet more preferably 35±3 mg/mL, most preferably 35±2 mg/mL, and in particular 35±1 mg/mL, based on the total volume of all aqueous phases within the composition.

In a preferred embodiment, the composition does not contain any preservative. For the purpose of this application, a "preservative" preferably refers to any substance that is usually added to pharmaceutical compositions in order to preserve them against microbial degradation or microbial growth. In this regard, microbial growth typically plays an essential role, i.e. the preservative serves the main purpose of avoiding microbial contamination. As a side aspect, it may also be desirable to avoid any effect of the microbes on the active ingredients and excipients, respectively, i.e. to avoid microbial degradation.

Representative examples of preservatives include benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

The complete absence of preservatives in the composition is preferred when the content of tapentadol is sufficiently high so that due to its preservative property the desired shelf life or in use stability can be achieved by the presence of the drug itself. Preferably, under these circumstances the concentration of tapentadol is at least 10 mg/mL, at least 12.5 mg/mL, at least 15 mg/mL, or at least 17.5 mg/mL, based on the total volume of the aqueous phase.

For the purpose of this application there is a distinction between shelf life and in-use stability. Shelf life preferably refers to the storage stability of a closed container of the pharmaceutical composition. In-use stability preferably refers to the storage container that contains a multiple dose preparation which has been utilized for the first time. Typically, the shelf-life of a multiple dose preparation is much longer than its in-use stability.

In another preferred embodiment, the composition additionally contains a preservative, which is preferably selected from the group consisting of benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

It has been surprisingly found that aqueous tapentadol compositions containing sodium benzoate show less total degradation products compared with aqueous tapentadol compositions containing parabens. Thus, sodium benzoate is a particularly preferred preservative according to the invention.

Preferably, the preservative is contained in such an amount that in absence of tapentadol would not sufficiently preserve the pharmaceutical composition according to the Ph. Eur.

Preferably, the content of the preservative is at most 5.0 wt.-%, more preferably at most 4.0 wt.-%, still more preferably at most 3.0 wt.-%, yet more preferably at most 2.0 wt.-%, most preferably at most 1.0 wt.-% and in particular at most 0.5 wt.-% or at most 0.2 wt.-%, based on the total weight of the aqueous phase.

It has been found that the antimicrobial effect of tapentadol, its preservative effect, is a function of the pH value. Thus, at a given pH value a certain minimum concentration of tapentadol is already sufficient in order to achieve the desired preserving effect, while at another pH value another minimum concentration of tapentadol is necessary in order to achieve the same preserving effect. This minimum concentration for a given pH value can be determined by routine experimentation.

In a preferred embodiment, the preservative, preferably benzoic acid or its sodium salt, has a concentration within the range of 1.0±0.6 mg/mL, more preferably 1.0±0.5 mg/mL, still more preferably 1.0±0.4 mg/mL, yet more preferably 1.0±0.3 mg/mL, most preferably 1.0±0.2 mg/mL, and in particular 1.0±0.1 mg/mL, based on the total volume of the aqueous phase.

In another preferred embodiment, the preservative, preferably benzoic acid or its sodium salt, has a concentration within the range of 1.5±0.6 mg/mL, more preferably 1.5±0.5 mg/mL, still more preferably 1.5±0.4 mg/mL, yet more preferably 1.5±0.3 mg/mL, most preferably 1.5±0.2 mg/mL, and in particular 1.5±0.1 mg/mL, based on the total volume of the aqueous phase.

In still another preferred embodiment, the preservative, preferably benzoic acid or its sodium salt, has a concentration within the range of 2.0±0.6 mg/mL, more preferably 2.0±0.5 mg/mL, still more preferably 2.0±0.4 mg/mL, yet more preferably 2.0±0.3 mg/mL, most preferably 2.0±0.2 mg/mL, and in particular 2.0±0.1 mg/mL, based on the total volume of the aqueous phase.

In yet another preferred embodiment, the preservative, preferably benzoic acid or its sodium salt, has a concentration within the range of 2.5±0.6 mg/mL, more preferably 2.5±0.5 mg/mL, still more preferably 2.5±0.4 mg/mL, yet more preferably 2.5±0.3 mg/mL, most preferably 2.5±0.2 mg/mL, and in particular 2.5±0.1 mg/mL, based on the total volume of the aqueous phase.

The additional presence of a preservative in the composition is preferred when the content of tapentadol is too low so that due to its preservative property the desired shelf life or in use stability cannot be achieved by the presence of the drug itself. As already mentioned above, the preservative property of tapentadol is a function of the pH value and thus, at one pH value the addition of another preservative might be necessary, whereas at another pH value it can be completely omitted. Preferably, under these circumstances the concentration of tapentadol is at most 12.5 mg/mL, at most 10 mg/mL, at most 8.0 mg/mL, at most 7.5 mg/mL, at most 5.0 mg/mL, at most 4.0 mg/mL, at most 3.0 mg/mL or at most 2.5 mg/mL, based on the total volume of the aqueous phase.

In a preferred embodiment, the relative weight ratio of tapentadol to the preservative is within the range of from 10:1 to 0.25:1, more preferably 9:1 to 0.33:1, still more preferably 8:1 to 0.5:1, yet more preferably 7:1 to 0.66:1, most preferably 6:1 to 0.75:1 and in particular 5:1 to 1:1. Preferably, the relative weight ratio of tapentadol to the preservative is within the range of from 5:1 to 1:1, more preferably 4.5:1 to 1:1, still more preferably 4:1 to 1:1, yet more preferably 3.5:1 to 1:1, most preferably 3:1 to 1:1 and in particular 2.5:1 to 1:1.

Preferably, the sum of the concentration of tapentadol and the concentration of preservative is below 30 mg/mL, based on the total volume of the aqueous phase.

In a preferred embodiment, the sum of the concentration of tapentadol and the concentration of preservative is within the range of 20±15 mg/mL, more preferably 20±17.5 mg/mL, still more preferably 20±15 mg/mL, yet more preferably 20±10 mg/mL, most preferably 20±7.5 mg/mL, and in particular 20±5 mg/mL, based on the total volume of the aqueous phase.

In another preferred embodiment, the sum of the concentration of tapentadol and the concentration of preservative is within the range of 15±12.5 mg/mL, more preferably 15±10 mg/mL, still more preferably 15±7.5 mg/mL, yet more preferably 15±5 mg/mL, and most preferably 15±3 mg/mL, and in particular 10±1 mg/mL, based on the total volume of the aqueous phase.

In still another preferred embodiment, the sum of the concentration of tapentadol and the concentration of preservative is within the range of 10±8 mg/mL, more preferably 10±6 mg/mL, still more preferably 10±4 mg/mL, yet more preferably 10±3 mg/mL, most preferably 10±2 mg/mL, and in particular 10±1 mg/mL, based on the total volume of the aqueous phase.

In a preferred embodiment, the content of the preservative is at most 90%, more preferably at most 80%, still more preferably at most 70%, yet more preferably at most 60%, most preferably at most 50% and in particular at most 40% of the content that would be needed according to Ph. Eur. in order to sufficiently preserve the pharmaceutical composition in the absence of tapentadol, either concerning its shelf-life or, in case of multiple dose preparations, optionally concerning its in-use stability. The criteria for sufficient preservation according to Ph. Eur. are met, if (a) the concentrations of viable bacteria are reduced to not more than 0.1% of the initial concentrations by the fourteenth day; and (b) the concentration of each test microorganism remains at or below these designated levels during the remainder of the 28-day test period. These criteria are more specifically defined in the experimental section. Preferably, after 2 days a log 2 reduction is achieved, after 7 days a log 3 reduction is achieved, and thereafter no increase can be observed.

Preferably, the composition according to the invention exhibits an antimicrobial robustness that complies with the requirements of the Ph. Eur., preferably in its version for 2010. Preferably, antimicrobial robustness is achieved against *E. coli, S. aureus, Ps. Aeruginosa,* S. spp., *C. albicans,* and/or *A. niger,* preferably satisfying the requirement of log reduction of 1, preferably 3 after 14 and no increase after 28 days. In a particularly preferred embodiment, antimicrobial robustness is achieved against bacteria satisfying the requirement of log reduction of 3 after 14 days and against molds and yeast of log reduction of 1 after 14 days.

Preferably, the composition according to the invention exhibits a shelf-life under accelerated storage conditions of at least 1 month, more preferably at least 2 months, still more preferably at least 3 months, yet more preferably at least 4 months, most preferably at least 5 months and in particular at least 6 months. Preferably, the shelf life is determined according to Ph. Eur., particularly as described in the experimental section. Accelerated storage conditions preferably mean 40±2° C./75% relative humidity.

Preferably, the composition according to the invention exhibits a shelf-life under ambient conditions of at least 6 month, more preferably at least 12 months, still more preferably at least 15 months, yet more preferably at least 18 months, most preferably at least 21 months and in particular at least 24 months.

Preferably, the composition according to the invention is a multiple dose preparation that exhibits an in-use stability under ambient conditions of at least 1 week, more preferably at least 2 weeks, still more preferably at least 3 weeks, yet more preferably at least 4 weeks, most preferably at least 5 weeks and in particular at least 6 weeks.

Preferably, the composition according to the invention further contains at least one lipid. In one preferred embodiment, the composition contains one lipid. In another preferred embodiment, the composition contains a mixture of at least two lipids.

In a preferred embodiment, the lipid is selected from the group consisting of
- saturated $C_8$ to $C_{18}$ fatty acids, such as myristic acid and stearic acid;
- unsaturated $C_8$ to $C_{18}$ fatty acids and their esters, such as oleic acid and ethyl oleate;
- mixtures of saturated and unsaturated $C_8$ to $C_{18}$ fatty acids, including vegetable oils such as soybean oil and peanut oil; hydrogenated oils such as hydrogenated castor oil; and animal fats; and
- glycerides of fatty acids, including monoglycerides, diglycerides, triglycerides, and mixtures thereof; preferably of $C_6$ to $C_{12}$ fatty acids, more preferably of $C_6$ to $C_{10}$ fatty acids, such as the caprylic/capric triglyceride mixtures, most preferably medium-chain triglycerides according to Ph. Eur. or USP, e.g. known and commercially available under the trade names "Captex®" and "Miglyol®";
- propylene glycol fatty acid esters such as propylene glycol monocaprylate (known and commercially available under the trade name "Capryol®");
- waxes including wool wax, carnauba wax, bees wax and mixtures of saturated $C_{18}$ to $C_{32}$ hydrocarbons such as hard paraffin and soft paraffin (e.g. white petroleum jelly).

Preferably, the lipid is a $C_8$-$C_{18}$-fatty acid ester of a monoalcohol (e.g. $C_1$-$C_{12}$-alkylalcohols), a di-$C_8$-$C_{18}$-fatty acid ester of a dialcohol (e.g. ethylene glycol or propylene glycol) or tri-$C_8$-$C_{18}$-fatty acid ester of a trialcohol (e.g. glycerol). Especially preferred are medium-chain triglycerides according to Ph. Eur. or USP such as said caprylic/capric triglyceride mixtures.

Preferably, the content of the lipid in the composition is within the range of from 0.1 wt.-% to 90 wt.-%, preferably from 1 wt.-% to 80 wt.-%, more preferably from 5 wt.-% to 70 wt.-%, still more preferably from 10 wt.-% to 50 wt.-%, yet more preferably from 15 wt.-% to 45 wt.-%, and most preferably from 20 wt.-% to 40 wt.-%, based on the content of all lipids contained in the composition.

In a preferred embodiment, the lipid is semisolid or solid at room temperature; i.e. the lipid is a wax or hard fat. Preferably, the semisolid or solid lipid has a melting point of at most 100° C., more preferably of at most 95° C., still more preferably of at most 90° C., and most preferably of at most 85° C., even more preferably of at most 80° C., and most preferably of at most 75° C.

In another preferred embodiment, the lipid is liquid at room temperature; i.e. the lipid is an oil. Preferably, the oil has a density within the range of 0.94±0.07 g/cm$^3$, more preferably 0.94±0.06 g/cm$^3$, still more preferably 0.94±0.05 g/cm$^3$, yet more preferably 0.94±0.04 g/cm$^3$, even more preferably 0.94±0.03 g/cm$^3$, most preferably 0.94±0.02 g/cm$^3$, and in particular 0.94±0.01 g/cm$^3$. Preferably, the pure oil has a viscosity at 20° C. measured in accordance with Ph.Eur. 2.2.8, within the range of 30±9 mPas, more preferably 30±8 mPas, still more preferably 30±7 mPas, yet more preferably 30±6 mPas, even more preferably 30±5 mPas, most preferably 30±4 mPas, and in particular 30±3 mPas.

In an especially preferred embodiment, the composition contains both an oil and a wax. For example, the composition may contain a liquid triglyceride mixture and soft paraffin. Preferably, the relative weight ratio of the oil to wax is within the range of from 30:1 to 1:30, more preferably 20:1 to 1:20, still more preferably 10:1 to 1:15, yet more preferably 5:1 to 1:10, most preferably 1:1 to 1:7.5 and in particular 1:2 to 1:5.

Preferably, the composition according to the invention further contains a surfactant. The surfactant may act as an emulsifier, wetting agent, solubiliser and/or detergent. In one preferred embodiment, the surfactant acts as an O/W emulsifier. In another preferred embodiment, the surfactant acts as a W/0 emulsifier.

In a preferred embodiment, the composition contains a single surfactant. In another preferred embodiment, the composition contains a mixture of two or more surfactants.

Preferably, the surfactants contained in the composition have a weighted average HLB value of at least 10, in particular a HLB value within 11 and 14.

The surfactant may be an ionic surfactant, amphoteric surfactant or non-ionic surfactant.

In a preferred embodiment, the surfactant is ionic, in particular anionic. Suitable anionic ionic surfactants include but are not limited to sodium lauryl sulfate (sodium dodecyl sulfate), sodium cetyl stearyl sulfate, sodium dioctylsulfosuccinate (docusate sodium); and the corresponding potassium or calcium salts thereof.

In another preferred embodiment, the surfactant is cationic. Suitable cationic ionic surfactants include but are not limited to quaternary ammonium compounds, such as benzalkonium chloride, benzethonium chloride, cetylpyridinium chloride, cetyl trimethylammoniom bromide, cetyl trimethylammoniom chloride, 5-bromo-5-nitro-1,3-dioxane, dimethyldioctadecylammonium chloride and dimethyldioctadecylammonium bromide; and hydrohalide salts of amines, such as octenidine dihydrochloride.

In still another preferred embodiment, the surfactant is amphoteric. Suitable amphoteric surfactants include the group of phospholipids, e.g. lecithine.

In yet another preferred embodiment, the surfactant is non-ionic. Suitable non-ionic surfactants include but are not limited to
  polyoxyethylene-sorbitan-fatty acid esters, e.g. mono- and tri-lauryl, palmityl, stearyl and oleyl esters, such as the type known under the name "polysorbat" and commercially available under the trade name "Tween®" including the surfactants tween 20 [polyoxyethylene(20)sorbitan monolaurate], tween 40 [polyoxyethylene(20)sorbitan monopalmitate], 60 [polyoxyethylene(20)sorbitan monostearate], tween 65 [polyoxyethylene(20)sorbitan tristearate], tween 80 [polyoxyethylene(20)sorbitan monooleate], tween 85 [polyoxyethylene(20)sorbitan trioleate], tween 21 [polyoxyethylene(4)sorbitan monolaurate] and tween 81 [polyoxyethylene(5)sorbitan monooleate];
  polyoxyethylene-glycerol-fatty acid esters, e.g. mono- and tri-lauryl, palmityl, stearyl and oleyl esters, such as the type known and commercially available under the trade name "Tagat®"
  polyoxyethylene fatty acid esters, the fatty acid preferably having from about 8 to about 18 carbon atoms, such as diglycol stearate, glycol stearate, glycol distearate and mixtures of polyoxyethylene esters of 12-hydroxystearic acid, such as the type known and commercially available under the trade name "Solutol®";
  polyoxyethylene esters of alpha-tocopheryl succinate, e.g. D-alpha-tocopheryl-PEG-1000-succinate (TPGS);
  polyglycolyzed glycerides, such as the types known and commercially available under the trade names "Gelucire®" and "Labrasol®";
  reaction products of a natural or hydrogenated castor oil and ethylene oxide such as the various liquid surfactants known and commercially available under the trade name "Cremophor®";
  glycerol fatty acid esters, e.g. mono- and tri-lauryl, palmityl, stearyl and oleyl esters, including diglycol stearate, glycerol monostearate, glycerol monopalmitate and glycerol trioleate;
  fatty alcohols or sterols including cetyl alcohol, stearyl alcohol, cetylstearyl alcohol and cholesterol.

In a particularly preferred embodiment, the pharmaceutical composition according to the invention comprises a surfactant or mixture of different surfactants obtainable by esterifying saturated or unsaturated $C_{12}$-$C_{18}$-fatty acids, optionally bearing a hydroxyl group, with glycerol and optionally, a polyethylene glycol; wherein the polyethylene glycol preferably comprises 10 to 40 ethylene oxide units ($-CH_2CH_2O-$). Especially preferred surfactants that are contained in the composition according to the invention are non-ionic surfactants having a hydrophilic-lipophilic balance (HLB) of at least 10, in particular non-ionic surfactants having an HLB value of at least 12, more in particular non-ionic surfactant's having an HLB value within 14 and 16. Examples for this type of surfactants are the surfactants "Tween® 80", "Solutol® HS 15" and "Tagat® S2".

In another preferred embodiment the pharmaceutical composition according to the invention contains at least one surfactant having a HLB value of at least 10 (hydrophilic surfactant) and at least one surfactant having a HLB value below 10 (lipophilic surfactant). For example, the composition may contain macrogol-20-glycerolhydroxystearat 40 (e.g., Tagat® S2) and/or cetyl alcohol as the hydrophilic surfactant component and glycerol monostearate as the lipophilic surfactant component.

Preferably, the hydrophilic surfactant is selected from
  the group consisting of macrogolhydroxystearate, macrogolglycerylhydroxystearate and macrogolglyceryllaurate, wherein the macrogol moiety preferably comprises 15 to 45 ethylene oxide units; and/or
  the group consisting of cetyl alcohol, stearyl alcohol and cetylstearyl alcohol.

Preferably, the lipophilic surfactant is selected from the group consisting of glycerol monostearate, glycerol monopalmitate and glycerol trioleate.

Preferably, the relative weight ratio of the surfactant having a HLB value of at least 10 (hydrophilic surfactant) and the surfactant having a HLB value below 10 (lipophilic surfactant) is greater than or equal to 1.

Preferably, the relative weight ratio of the surfactant having a HLB value of at least 10 (hydrophilic surfactant) and the surfactant having a HLB value below 10 (lipophilic surfactant) is within the range of 20:1 to 1:15, more preferably 15:1 to 1:10, still more preferably 12:1 to 1:8, yet more preferably 10:1 to 1:6, even more preferably 7:1 to 1:5, most preferably 5:1 to 1:2 and in particular 4:1 to 1:1.

In a preferred embodiment, the content of the surfactant is at least 0.1 wt.-%, more preferably at least 1 wt.-%, still more preferably at least 2 wt.-%, or at least 3 wt.-%, yet more preferably at least 5 wt.-%, or at least 7 wt.-%, most preferably at least 10 wt.-%, or at least 12 wt.-%, and in particular at least 14 wt.-%, or at least 15 wt.-%, based on the total weight of the composition.

In a preferred embodiment, the content of the surfactant ranges preferably from 0.1 wt.-% to 95 wt.-%, more preferably from 1 wt.-% to 80 wt.-%, still more preferably from 2.5 wt.-% to 70 wt.-%, yet more preferably from 5 wt.-% to 50 wt.-%, most preferably from 7.5 wt.-% to 30 wt.-%, and in particular from 10 wt.-% to 25 wt.-%, based on the total weight of the composition.

In a preferred embodiment, the relative weight ratio of the surfactant to the lipid is within the range of from 20:1 to 1:20, more preferably 10:1 to 1:10, still more preferably 7.5:1 to 1:5, yet more preferably 6:1 to 1:2, most preferably 5:1 to 1:1 and in particular 3.5:1 to 1.5:1.

The composition according to the invention may further contain a hydrophilic solvent. The hydrophilic solvent may be selected from the group consisting of propylene glycol, ethanol, poly(ethylene glycol) or PEG, propylene carbonate, diethylene glycol monoethyl ether, poloxamer, glycofurol, glycerol, and mixtures thereof.

The composition according to the invention may be buffered, i.e. contains one or more buffers and buffer systems (i.e. conjugate acid-base-pairs), respectively. Preferred buffer systems are derived from the following acids: organic acids such as acetic acid, propionic acid, maleic acid, fumaric acid, malonic acid, malic acid, mandelic acid, citric acid, tartric acid; or inorganic acids such as phosphoric acid, or organic bases such as trometamol. Buffer systems derived from citric acid, phosphoric acid or trometamol are particularly preferred. When the buffer systems are derived from any of the above acids, the buffer system constitutes of said acid and its conjugate base.

Persons skilled in the art will be aware that multiprotonic acids can form more than a single buffer system. For example, citric acid is a triprotonic acid so that it forms the conjugate acid-base pairs citric acid-dihydrogencitrate, dihydrogencitrate-hydrogencitrate and hydrogencitrate-citrate. In other words, any of citric acid, dihydrogencitrate and hydrogencitrate can be the acid of a buffer system with the conjugate base. For the purpose of this application, the expression "buffer and buffer system, respectively" preferably refers to the quantity of both, the acid and its conjugate base. Further, a skilled person is fully aware that a buffer system, e.g. the conjugate system citric acid/sodium dihydrogencitrate can be established either by adding citric acid and an appropriate amount of sodium hydroxide or citric acid and sodium dihydrogencitrate as such.

Liquid and semisolid compositions can be characterized by their viscosity and flow behavior and classified as follows.

Newtonian fluids exhibit ideal flow characteristics; i.e. the relation between shear stress and shear rate is linear and their viscosity does thus not depend on the shear rate. Pure liquids usually exhibit Newtonian fluid characteristics.

Most semisolid compositions, however, show a non-linear relation between shear stress and shear rate. They are referred to as non-Newtonian fluids or structurally viscous fluids. According to their different correlations between shear stress and shear rate, they are classified as pseudoplastic, dilatant fluid, Bingham plastic or Casson plastic.

Pseudoplastic fluids exhibit a decreasing viscosity as the applied shear rate is increased. Examples are creams that contain anisometric solid particles.

Dilatant fluids exhibit an increasing viscosity as the applied shear rate is increased. Examples of this type are pastes having a high content of solid material.

Plastic fluids are not able to flow at low shear stresses. However, after a certain shear stress value, the so-called shear stress yield, has been reached, they may show an ideal plastical flow behavior (Bingham plastic fluid) or non-ideal flow behavior (Casson plastic fluid). Examples are gels in which the polymeric structure formed by the gelling agent has to be broken by a certain amount of shear stress before flowing may occur. Once the structure has been broken and the shear stress is further increased, the fluid may for example behave as a liquid and exhibit Newtonian characteristics. Once the shear stress is removed, the fluid usually regains its plastic flow characteristics, most often, however, with time lag (thixotropic fluid).

Fluids may also show a combination of the above-mentioned flow characteristics. For example, a fluid may exhibit a Newtonian fluid behavior at low shear stresses and a pseudoplastic fluid behavior at high shear stresses.

The viscosity and flow behavior of a liquid or semisolid composition can be experimentally determined by means of a rotational viscosimeter.

Preferably, the composition according to the invention exhibits a viscosity of a most $10^{12}$ mPa·s, more preferably of at most $10^{10}$ mPa·s, still more preferably of at most $10^9$ mPa·s, yet more preferably of at most $10^8$, most preferably of at most $10^7$ mPa·s, and in particular of $10^6$ mPa·s. In a preferred embodiment, the viscosity is within the pange of from 1 to 100 Pa·s, more preferably 5 to 20 Pa·s, when measured in accordance with Eur. Ph. In a preferred embodiment, the composition according to the invention exhibits Newtonian fluid characteristics.

In another preferred embodiment, the composition exhibits non-Newtonian fluid characteristics.

Preferably, the semisolid composition is selected from the group of pseudoplastic fluids, dilatant fluids and plastic fluids.

In a preferred embodiment, the semisolid composition exhibits the fluid characteristics of a dilatant fluid.

In another preferred embodiment, the semisolid composition exhibits the fluid characteristics of a plastic fluid. The plastic fluid may be a Bingham plastic fluid or a Casson plastic fluid. Preferably, the plastic fluid also exhibits viscoelastic properties.

In still another preferred embodiment, the semisolid composition exhibits the fluid characteristics of a pseudoplastic fluid. Preferably, the viscosity curve of the pseudoplastic fluid resembles the one of a Newtonian at low shear stresses and/or at high shear stresses.

Preferably, at low shear stresses of at most 50 Pa and 25° C., the viscosity does not change by at most 40%, more preferably at most 30%, still more preferably at most 20%, most preferably at most 10%.

Preferably, at low shear stresses of at most 100 Pa and 25° C., the viscosity does not change by at most 40%, more preferably at most 30%, still more preferably at most 20%, most preferably at most 10%.

Preferably, at a shear rate of 40 s$^{-1}$ and 25° C., the composition exhibits a viscosity within the range of from 1 mPa·s to $1·10^{12}$ mPa·s, more preferably within the range of from 2 mPa·s to $1·10^{11}$ mPa·s, still more preferably within the range of from 5 mPa·s to $1·10^{10}$ mPa·s, yet more preferably within the range of from 10 mPa·s to $1·10^9$ mPa·s, most preferably within the range of from 50 mPa·s to $1 \cdot 10^6$ mPa·s, and in particular within the range of from $10^2$ mPa·s to $1 \cdot 10^4$ mPa·s.

Preferably, at a shear rate of 80 s$^{-1}$ and 25° C., the composition exhibits a viscosity within the range of from 1 mPa·s to $1 \cdot 10^{12}$ mPa·s, more preferably within the range of from 2 mPa·s to $1 \cdot 10^{11}$ mPa·s, still more preferably within the range of from 5 mPa·s to $1 \cdot 10^{10}$ mPa·s, yet more preferably within the range of from 10 mPa·s to $1 \cdot 10^9$ mPa·s, most preferably within the range of from 50 mPa·s to $1 \cdot 10^6$ mPa·s, and in particular within the range of from $10^2$ mPa·s to $1 \cdot 10^4$ mPa·s.

Preferably, at a shear rate of 120 s$^{-1}$ and 25° C., the composition exhibits a viscosity within the range of from 1 mPa·s to $1 \cdot 10^{12}$ mPa·s, more preferably within the range of from 2 mPa·s to $1 \cdot 10^{11}$ mPa·s, still more preferably within the range of from 5 mPa·s to $1 \cdot 10^{10}$ mPa·s, yet more preferably within the range of from 10 mPa·s to $1 \cdot 10^9$ mPa·s, most preferably within the range of from 50 mPa·s to $1 \cdot 10^6$ mPa·s, and in particular within the range of from $10^2$ mPa·s to $1 \cdot 10^4$ mPa·s.

Preferably, at a shear rate of 160 s$^{-1}$ and 25° C., the composition exhibits a viscosity within the range of from 1 mPa·s to $1 \cdot 10^{12}$ mPa·s, more preferably within the range of from 2 mPa·s to $1 \cdot 10^{11}$ mPa·s, still more preferably within the range of from 5 mPa·s to $1 \cdot 10^{10}$ mPa·s, yet more preferably within the range of from 10 mPa·s to $1 \cdot 10^9$ mPa·s, most preferably within the range of from 50 mPa·s to $1 \cdot 10^6$ mPa·s, and in particular within the range of from $10^2$ mPa·s to $1 \cdot 10^4$ mPa·s.

In a preferred embodiment, at a shear rate of 40 s$^{-1}$ and 25° C., the composition exhibits a viscosity of preferably at least 4,850 mPa·s, more preferably of at least 4,900 mPa·s, still more preferably of at least 4,950 mPa·s, yet more preferably of at least 5,000 mPa·s, most preferably of at least 5,100 mPa·s, and in particular of at least 5,200 mPa·s.

In a preferred embodiment, at a shear rate of 80 s$^{-1}$ and 25° C., the composition exhibits preferably a viscosity of at least 2,250 mPa·s, more preferably of at least 2,300 mPa·s, still more preferably of at least 2,350 mPa·s, yet more preferably of at least 2,400 mPa·s, most preferably of at least 2,450 mPa·s, and in particular of at least 2,500 mPa·s.

In a preferred embodiment, at a shear rate of 120 s$^{-1}$ and 25° C., the composition exhibits a viscosity of preferably at least 1,600 mPa·s, more preferably of at least 1,650 mPa·s, still more preferably of at least 1,700 mPa·s, yet more preferably of at least 1,750 mPa·s, most preferably of at least 1,800 mPa·s, and in particular of at least 1,850 mPa·s.

In a preferred embodiment, at a shear rate of 160 s$^{-1}$ and 25° C., the composition exhibits a viscosity of preferably at least 1,300 mPa·s, more preferably of at least 1,350 mPa·s, still more preferably of at least 1,400 mPa·s, yet more preferably of at least 1,450 mPa·s, and most preferably of at least 1,500 mPa·s.

The composition according to the invention may be transparent, translucent or opaque.

In a preferred embodiment, the composition is translucent having a visible light transmission of least 10%, more preferably of at least 20%, even more preferably of at least 30%, yet more preferably of at least 50%, still more preferably of at least 70%, most preferably of at least 80%, and in particular of at least 90%.

In a preferred embodiment, the composition is translucent having a visible light transmission of at most least 90%, more preferably of at most 80%, even more preferably of at most 70%, yet more preferably of at most 50%, still more preferably of at most 30, most preferably of at most 20%, and in particular of at most 10%.

The compositions may include one or more further excipients selected from the group consisting of thickening agents, gelling agents, antioxidants, fragrances, chelating agents and penetration enhancers.

A thickening agent, viscosity-enhancing agent or gelling agent can be included to generally thicken the liquid composition. While any suitable thickening agent can be included in the compositions of the present invention, a preferred thickening agent, when used, includes one or more of acacia, alginic acid bentonite, carboxymethylcellulose calcium or sodium, cetostearyl alcohol, methyl cellulose, ethylcellulose, glycerin, gelatin, guar gum, hydroxyethylcellulose, hydroxypropylcellulose, hydroxypropylmethylcellulose, locust bean gum, maltodextrin, pectin, polyacrylic acid and its derivatives (carbomers), polyvinyl alcohol, polyvinylpyrrolidone, povidone, propylene carbonate, propylene glycol alginate, sodium alginate, sodium starch glycolate, starch, highly dispersed silicium dioxide, tragacanth, tragant and xanthan gum, and any combination thereof. More preferred thickening agents are carbomer, cellulose derivatives such as sodium carboxymethyl cellulose and methyl cellulose, galactomannans such as guar gum and locust bean gum, sodium alginate, and any combination thereof. Such a thickening agent, if present, will typically form about 0.1 wt.-% to 20 wt.-%, preferably about 0.3 wt.-% to about 15 wt.-%, and more preferably about 0.5 wt.-% to 4 wt.-%, of the total weight of the composition.

Examples of a suitable antioxidant component, if used, include one or more of the following: sulfites; ascorbic acid; ascorbates, such as sodium ascorbate, calcium ascorbate, or potassium ascorbate; ascorbyl palmitate; fumaric acid; ethylene diamine tetraacetic acid (EDTA) or its sodium or calcium salts; tocopherol; gallates, such as propyl gallate, octyl gallate, or dodecyl gallate; vitamin E; butylated hydroxyanisole (BHA), butylated hydroxytoluene (BHT), and mixtures thereof. Addition of the antioxidant component can help enhance and ensure the stability of the composition and render the composition stable even after six months at 40° C. A suitable amount of the antioxidant component, if present, is about 0.01 wt.-% to about 3 wt.-%, preferably about 0.05 wt.-% to about 2 wt.-%, of the total weight of the composition.

The composition according to the invention may further contain a fragrance. Suitable fragrances include lavender oil, rose oil, lemon oil and almond oil.

Examples of a suitable chelating agent, if used, include citric acid, maleic acid and ethylenediaminetetraacetic acid (EDTA) and its sodium or caclium salts.

The composition according to the invention may contain a penetration enhancer that improves the transdermal drug delivery. Suitable penetration enhancers include cyclodextrins, ethanol, oleic acid, lecithin, propylene glycol, Fatty acid esters of propylene glycol (e.g. propylene glycol dipelargonate), polyethylene glycole, and terpenes such as nerolidol, geraniol, carvacrol, eucalyptol, menthol, limonene, linalool and cineol.

Preferably, the pharmaceutical composition is for the treatment of acute or chronic pain.

In a preferred embodiment, the pain is related to wounds, burns, ulcers or abcesses of the skin and/or mucous membranes.

In another preferred embodiment, the pain is related to bone disorders, joint disorders and/or muscle disorders.

Preferably, the pain is related to rheumatic disorders, arthritic disorders, painful joints, postoperative complaints, dental surgery, skin inflammation (dermatitis), skin lesions, skin cancer, mouth sores and/or athletic injuries.

In a preferred embodiment, administration of the composition proceeds topically and/or locally. In this regard, topical and/or local administration includes every administration of the composition to a site which is identical to the site of pain and/or at least is located nearby. In particular, the topical and/or local administration has the purpose of delivering tapentadol directly to the desired site of action, thereby avoiding systemic side-effects.

Preferably, the systemic concentration of tapentadol is kept at a sub-therapeutic concentration; i.e. during the treatment, the systemic concentration of tapentadol never reaches the level that is required for exhibiting a therapeutic effect when the drug is only applied systemically.

The composition may be applied topically to the skin, cornea, rectal tissue, nasal mucosa, vagina, buccal tissue, urethral membrane and/or external ear lining.

In another preferred embodiment, the administration of the composition has the purpose of inducing a systemic mode of action.

Preferably, the composition according to the invention is adapted for administration once daily, twice daily, thrice daily, four times daily, five times daily, six times daily or even more frequently.

In a preferred embodiment the composition according to the invention is adapted for administration to pediatric, geriatric and/or pregnant patients.

For the purpose of this application, pediatric patients preferably encompass infants, children, and adolescents. Preferably the upper age limit of such patients is 12, 13, 14, 15, 16, 17, 18, 19, 20 or 21.

For the purpose of this application, geriatric patients preferably encompass patients with a lower age limit of 60, preferably 62, more preferably 64, even more preferably 66, yet more preferably 68, and in particular 70.

In this regard the surprising preservative properties of tapentadol are even more beneficial, as the drug approval authorities have recommended stricter standards as to the presence of preservative in medicaments for pediatric patients. Further, as tapentadol is suitable for treating pain in patients suffering from serious diseases, e.g. for treating cancer pain, such patients including pediatric patients are usually simultaneously treated with other medicaments, e.g. chemotherapeutics, that have severe side effects. Under these circumstances, it is even more desirable to not expose such pediatric patients to preservatives, if avoidable.

In this regard the topical and/or local treatment of pain is also beneficial, since the systemic concentration of tapentadol may be kept at a sub-therapeutic level and systemic side effects that burden the entire organism may be avoided. To keep the systemic concentration of a drug at a low level is especially crucial in the treatment of particularly pediatric, geriatric and/or pregnant patients.

Preferably, the composition is a multiple dose form, i.e. customized for more than a single administration. For the purpose of this application, "multiple dose" preferably means that the composition encompasses more than a single dosage unit. For example, when the composition is a multiple dose cream, its overall volume is more than the volume that is to be typically administered at once. Instead, the multiple dose cream is customized for being divided into a multitude of dosage units that are to be administered over a treatment interval typically encompassing several days. For example, when the multiple dose composition that is contained in a storage container has a total volume of 20 mL and the prescribed dosage unit approx. 2 mL once daily, at day 1 of the treatment interval the patient takes 2 mL so that 18 mL remain in the storage container; at day 2 of the treatment interval the patient takes another 2 mL so that 16 mL remain in the storage container; and so on, until at day 10 the entire amount is taken by the patient.

In a preferred embodiment, the semisolid aqueous composition according to the invention is ready to use, i.e. does not require particular treatment steps such as dispersing in a liquid medium before it may be administered to the patient.

Persons skilled in the art will recognize that the aqueous semisolid composition according to the invention may alternatively be commercialized as a precursor in form of a dry powder that is to be dispersed in an appropriate amount of water prior to the first use.

A further aspect of the invention relates to a pharmaceutical dosage form comprising the pharmaceutical composition according to the invention. All preferred embodiments that are described above in connection with the composition according to the invention also apply to the dosage form according to the invention.

A still further aspect of the invention relates to the use of tapentadol for the manufacture of the pharmaceutical composition according to the invention as described above or of the pharmaceutical dosage form according to the invention as described above for the treatment of pain.

In a preferred embodiment, the composition is made by melting its semisolid and/or solid ingredients, optionally in presence of other ingredients, and mixing them with the remaining ingredients to form a homogeneous mixture.

In another preferred embodiment, the composition is made by separately preparing
- the aqueous phase containing the tapentadol, water and preferably a surfactant; and
- the lipid phase containing the lipid, and optionally other ingredients such as surfactants, waxes and/or lubricants;

and mixing the two phases thereafter, preferably at an increased temperature at which both phases are liquid.

In still another preferred embodiment, the composition is prepared by triturating two or more of the ingredients.

In yet another preferred embodiment, the composition is prepared by means of an ointment mill.

A yet further aspect of the invention relates to a method for the treatment of pain comprising the topical and/or local administration of the pharmaceutical composition according to the invention as described above or of the pharmaceutical dosage form according to the invention as described above to a subject in need thereof.

In a particular preferred embodiment, the composition according to the invention is a composition:
- wherein the content of tapentadol is within the range of from 0.01 to 50 wt.-%; and/or
- wherein the water content is at least 0.5 wt.-%; and/or
- which contains a surfactant having a HLB value of at least 10; and/or
- which contains a lipid, preferably a triglyceride; and/or
- which contains a wax selected from wool wax, carnauba wax, bees wax, hard paraffin, soft paraffin and white petroleum jelly;
- which does not contain any preservative; and/or which is a biphasic or multiple-phase system containing at least one aqueous and at least one lipid phase, and the aqueous phase is preferably a coherent phase; and/or which is a non-Newtonian fluid; and/or which exhibits the fluid characteristics of a pseudoplastic fluid; and/or which is adapted for topical and/or local administration; and/or which is adapted for administration to pediatric, geriatric and/or pregnant patients.

whose preparation includes melting of semisolid and/or solid ingredients.

EXAMPLES

The following examples further illustrate the invention but are not be construed as limiting its scope.

Example 1

Creams were formulated according to the following compositions.

TABLE 1

| Ingredients [wt.-%] | C-1 | I-1 | I-2 |
|---|---|---|---|
| Aqueous Phase | | | |
| Tapentadol HCl | 0.0 | 0.6 | 1.25 |
| Macrogol-20-glycerol-monostearate (Tagat S2) | 7.0 | 7.0 | 7.0 |
| Purified water | 50.0 | 49.4 | 48.75 |
| Lipid phase | | | |
| Glycerolmonostearate | 4.0 | 4.0 | 4.0 |
| Cetyl alcohol | 6.0 | 6.0 | 6.0 |
| Miglyol ® 812 | 7.5 | 7.5 | 7.5 |
| White petroleum jelly | 25.5 | 25.5 | 25.5 |

In the creams the aqueous phase represented the coherent phase (o/w-type), so that the formulation should be principally sensitive to microbial contamination. The formulations were stored in amber glass container.

Assuming that tapentadol hydrochloride is only present in the aqueous phase, its concentration therein amounts to 12.0 mg/mL (10.3 mg/mL tapentadol) for the inventive formulation I-1 and 25.0 mg/mL (21.46 mg/mL tapentadol) for the inventive formulation I-2.

The formulations were spiked with *Staphylococcus aureus* (*Staph. aureus*), *Pseudomonas aeruginosa* (*Ps. aerouginosa*), *Aspergillus niger* (*Asp. niger*) and *Candida albicans* and their efficacy of antimicrobial preservation was evaluated according to the test "efficacy of antimicrobial preservation" as recommended by the Ph. Eur. The test acceptance criteria for the preparations according to the Ph. Eur. are given in Tables 2 and 3. The criteria A express the recommended efficacy to be achieved. In justified cases where the criteria A cannot be attained, for example for reasons of an increased risk of adverse reaction, the criteria B must be satisfied.

TABLE 2

Acceptance criteria for topical preparations ("Efficacy of antimicrobial preservation" test, Ph. Eur.)

| | | Log reduction | | | |
|---|---|---|---|---|---|
| | Test criteria | 2 d | 7 d | 14 d | 28 d |
| Bacteria | A | 2 | 3 | — | NI |
| | B | — | — | 3 | NI |
| Fungi | A | — | — | 2 | NI |
| | B | — | — | 1 | NI |

(NI = no increase, NR = no recover)

TABLE 3

Acceptance criteria for parenteral preparations ("Efficacy of antimicrobial preservation" test, Ph. Eur.)

| | | Log reduction | | | | |
|---|---|---|---|---|---|---|
| | Test criteria | 6 h | 24 h | 7 d | 14 d | 28 d |
| Bacteria | A | 2 | 3 | — | — | NR |
| | B | — | 1 | 3 | — | NI |
| Fungi | A | — | — | 2 | — | NI |
| | B | — | — | — | 1 | NI |

(NI = no increase, NR = no recover)

The "efficacy of antimicrobial preservation" tests revealed that the placebo cream did not show any preservative effect of the formulation itself. The antimicrobial effect of the formulation containing tapentadol HCl is thus a consequence of presence of tapentadol. Moreover, it was demonstrated that the efficacy of antimicrobial preservation depends on the amount of tapentadol; the inventive formulation I-1 containing 10.3 mg tapentadol per mL of the aqueous phase was preserved by tapentadol to a certain extent, but *Staph. aureus* (crit. A and B) and *Aps. niger* (crit. A) were not sufficiently reduced during the test time according to the test parameters. The inventive formulation I-2 (21.6 mg tapentadol per mL of the aqueous phase), however, was sufficiently preserved by tapentadol even for all tested bacteria/fungi.

Conclusion:

The experiments using different concentrations of tapentadol in the cream show that the concentration where the preservative effect of tapentadol starts is between 12 and 25 mg of tapentadol HCl in 100 mL of the aqueous phase. In a suitable concentration tapentadol can thus be used as a preservative for creams.

Example 2

Figure 1:
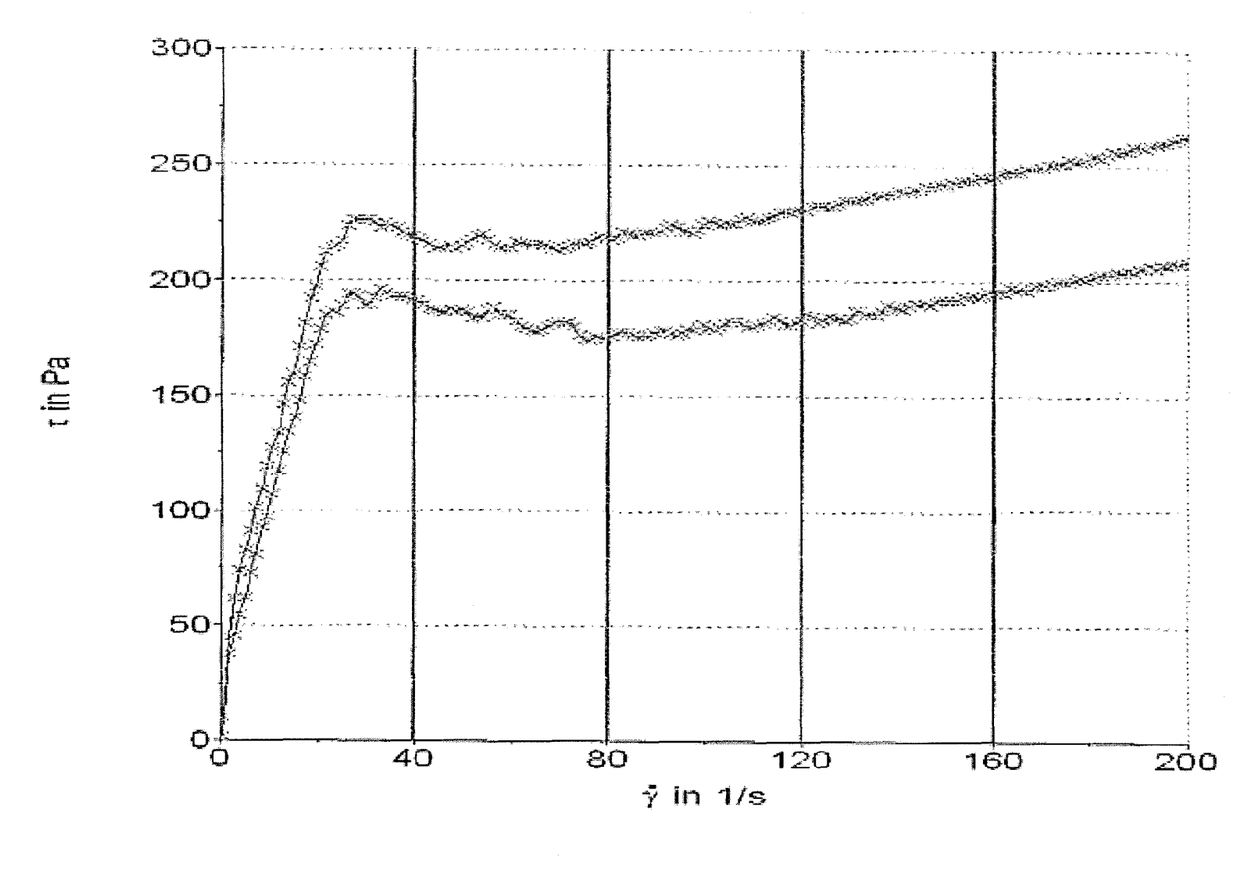
FIG. 1 is a graph showing the viscosity curves of semisolid compositions according to the invention measured at 25° C. by a rotational viscosimeter.

The viscosity curves of example compositions I-1 and I-2 according to the invention were determined as follows:

The experiments were conducted with a Haake RotoVisco RV1 device (sensor C60/1° together with thermocontroler DC30, Haake) at 25.0±0.1° C. The material (1.0 mL) was placed between the stator and the rotor and the gap distance of which was adjusted to 0.052 mm. The material was tempered at 25.0° C. before the experiment was started. The viscosity curve was determined with the software RheoWin 3 and the viscosity values (n=4) at different shear stresses ($\Delta$=40 s$^{-1}$) were taken to characterize the inventive samples. The viscosity curves are depicted in FIG. 1 and the calculated viscosity values are listed in the following table.

TABLE 4

| shear rate [1/s] | viscosity [mPa · s] | | shear stress [Pa] | | t [s] | |
|---|---|---|---|---|---|---|
| | I-1 | I-2 | I-1 | I-2 | I-1 | I-2 |
| 40.000 | 4790.6 | 5457.8 | 191.59 | 218.26 | 161.80 | 122.39 |
| 80.000 | 2189.0 | 2722.7 | 175.11 | 217.80 | 197.81 | 158.39 |
| 120.00 | 1532.3 | 1917.9 | 183.87 | 230.14 | 233.81 | 194.39 |
| 160.00 | 1219.2 | 1533.4 | 195.07 | 245.34 | 269.79 | 230.38 |

In both cases the viscosity decreased with increasing shear rate, i.e. both fluids exhibited a pseudoplastic flow behavior.

Example 3

Antimicrobial Effect of Tapentadol at pH 3 and pH 8

A tapentadol solution with a concentration of 15 mg/mL tapentadol (free base) was prepared. The pH-value was adjusted to the target value of 3 or 8 using citric acid and 1N NaOH solution, respectively. No additional buffer system was added. To ensure the placebo solution shows no antimicrobial effect itself, a placebo solution pH 8 was prepared, with focus on the same pH-value, even though a different amount of 1N NaOH solution was used for pH adjustment.

The formulations were prepared, filled in glass bottles and sterilized in an autoclave for 30 min at 121° C. and 2 bars. The sterilized glass bottles were spiked with *Staphylococcus aureus* (*Staph. aureus*), *Pseudomonas aeruginosa* (*Ps. aerouginosa*), *Aspergillus niger* (*Asp. niger*) and *Candida albicans* for the test "Efficacy of antimicrobial preservation" on the basis of Ph. Eur. 6.6 monograph 5.1.3. The Ph. Eur. test acceptance criteria for parenteral preparations are given in Table 1 (NI=no increase, NR=no recover). The A criteria express the recommended efficacy to be achieved, in justified cases where the A criteria cannot be attained for example for reasons of an increased risk of adverse reaction, the B criteria must be satisfied. To reduce the amount of experiments for this first set up of pH-value experiments, the test points at 6 and 24 hours were replaced by a test point at 30 min (table 5).

TABLE 5

Acceptance criteria for parenteral preparations for "Efficacy of antimicrobial preservation" (Ph. Eur.)
Log reduction

| | Test criteria | 6 h | 24 h | 7 d | 14 d | 28 d |
|---|---|---|---|---|---|---|
| Bacteria | A | 2 | 3 | — | — | NR |
| | B | — | 1 | 3 | — | NI |
| Fungi | A | — | — | 2 | — | NI |
| | B | — | — | — | 1 | NI |

The results for the microbial testing of the solutions are given for each bacteria/fungi in Tables 6 to 9.

TABLE 6

Microbial growth of *Staph. aureus*

| Microbial count | Placebo pH 8 | Tapentadol pH 8 | Tapentadol pH 3 |
|---|---|---|---|
| Spiked amount of bacteria/fungi | $7.4 \times 10^5$ | $1.7 \times 10^6$ | $1.6 \times 10^6$ |
| 30 min | $8.3 \times 10^5$ | $8 \times 10^5$ | $2.5 \times 10^6$ |

TABLE 6-continued

Microbial growth of *Staph. aureus*

| Microbial count | Placebo pH 8 | Tapentadol pH 8 | Tapentadol pH 3 |
|---|---|---|---|
| 7 days | $2.8 \times 10^5$ | $<\times 10^2$ | $2.3 \times 10^3$ |
| 14 days | not tested | $<\times 10^2$ | $<\times 10^2$ |
| 28 days | not tested | $<\times 10^2$ | $<\times 10^1$ |
| Test criteria A | failed | passed | passed |
| Test criteria B | failed | passed | passed |

TABLE 7

Microbial growth of *Ps. aeruginosa*

| Microbial count | Placebo pH 8 | Tapentadol pH 8 | Tapentadol pH 3 |
|---|---|---|---|
| Spiked amount of bacteria/fungi | $1.4 \times 10^6$ | $1.7 \times 10^6$ | $1.6 \times 10^6$ |
| 30 min | $1.6 \times 10^6$ | $<\times 10^4$ | $4.5 \times 10^5$ |
| 7 days | $8.8 \times 10^6$ | $<\times 10^2$ | $2 \times 10^3$ |
| 14 days | not tested | $<\times 10^2$ | $<\times 10^2$ |
| 28 days | not tested | $<\times 10^2$ | $<\times 10^2$ |
| Test criteria A | failed | passed | passed |
| Test criteria B | failed | passed | passed |

TABLE 8

Microbial growth of *Asp. niger*

| Microbial count | Placebo pH 8 | Tapentadol pH 8 | Tapentadol pH 3 |
|---|---|---|---|
| Spiked amount of bacteria/fungi | $4.2 \times 10^5$ | $5.4 \times 10^5$ | $3.9 \times 10^5$ |
| 30 min | $4.3 \times 10^5$ | $6 \times 10^5$ | $4.5 \times 10^5$ |
| 7 days | $6.3 \times 10^5$ | $4.5 \times 10^2$ | $8 \times 10^4$ |
| 14 days | not tested | $0.3 \times 10^2$ | $4.1 \times 10^5$ |
| 28 days | not tested | $1.8 \times 10^1$ | $4.5 \times 10^5$ |
| Test criteria A | failed | passed | failed |
| Test criteria B | failed | passed | failed |

TABLE 9

Microbial growth of *Candida albicans*

| Microbial count | Placebo pH 8 | Tapentadol pH 8 | Tapentadol pH 3 |
|---|---|---|---|
| Spiked amount of bacteria/fungi | $2 \times 10^5$ | $1.7 \times 10^5$ | $2.4 \times 10^5$ |
| 30 min | $2.5 \times 10^5$ | $<\times 10^4$ | $2 \times 10^5$ |
| 7 days | $3.4 \times 10^6$ | $<\times 10^2$ | $1.3 \times 10^3$ |
| 14 days | not tested | $<\times 10^2$ | $1.8 \times 10^3$ |
| 28 days | not tested | $<\times 10^2$ | $2.5 \times 10^3$ |
| Test criteria A | failed | passed | failed |
| Test criteria B | failed | passed | failed |

In the absence of additional preservatives, the tapentadol solution pH 3 is not sufficiently preserved according to Ph. Eur. (crit. A and B) for *Asp. niger* and *Cand. albicans*, whereas the tapentadol solution pH 8 passed the crit. A and B for all tested bacteria and funghi. The placebo pH 8 solution shows no preservative effect of the solution itself, so that the antimicrobial effect of the formulation containing tapentadol HCl is a consequence of the added amount of tapentadol HCl. Considering this results a clear dependency of the pH-value on the preserving effect of the tapentadol HCl solution could be shown.

The tapentadol HCl solution with a higher pH value of 8 has an improved antimicrobial effect compared to the pH 3 solution, so a clear dependency of the pH-value of the solution on the preserving effect of tapentadol was found.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A pharmaceutical composition comprising water and tapentadol or a physiologically acceptable salt thereof, wherein said composition is a semi-solid, and wherein the antimicrobial properties of tapentadol are sufficient such that the composition is either free of any preservative or, when the composition contains a preservative, the preservative is contained in an amount that in the absence of tapentadol would be insufficient to preserve the pharmaceutical composition according to Ph. Eur., and wherein said composition has an aqueous phase pH value of at least 5.5, and wherein said composition has a content of tapentadol within the range of from 0.1 to 40 wt.-%, based on the total weight of the composition.

2. The pharmaceutical composition according to claim 1, wherein said composition is adapted for topical or local administration.

3. The pharmaceutical composition according to claim 1, wherein said composition is selected from the group consisting of ointments, creams, magmas, gels, emulsions, suspensions, lotions, liniments, pastes, poultices, suspension gels and emulsion gels.

4. The pharmaceutical composition according to claim 1, wherein said composition is a bi-phasic formulation or a multi-phase formulation.

5. The pharmaceutical composition according to claim 1, wherein said composition has a tapentadol content amounting to at least 0.55 wt.-%, based on the total weight of the composition.

6. The pharmaceutical composition according to claim 1, wherein preservative content is at most 5.0 wt.-%, based on the total weight of the composition.

7. The pharmaceutical composition according to claim 1, wherein said composition further comprises at least one substance selected from the group consisting of lipids and surfactants.

8. The pharmaceutical composition according to claim 7, wherein said composition comprises a lipid selected from the group consisting of monoglycerides, diglycerides, triglycerides, and mixtures of two or more thereof.

9. The pharmaceutical composition according to claim 7, wherein said composition comprises a surfactant having an HLB value of at least 12.

10. The pharmaceutical composition according to claim 1, wherein said composition exhibits fluid characteristics of a pseudoplastic fluid.

11. The pharmaceutical composition according to claim 1, wherein said composition has a shelf-life under accelerated storage conditions of at least 3 months.

12. A method of treating pain in a subject in need thereof, said method comprising administering to said subject a pharamacologically effective amount of a semi-solid composition according to claim 1.

13. A method according to claim 12, wherein said pain is selected from the group consisting of chronic pain and acute pain.

14. A method according to claim 12, wherein said pain is related to rheumatic disorders, arthritic disorders, painful joints, postoperative complaints, dental surgery, dermatitis, skin lesions, skin cancer, mouth sores or athletic injuries.

* * * * *